United States Patent
Sun et al.

(10) Patent No.: US 8,218,839 B2
(45) Date of Patent: Jul. 10, 2012

(54) AUTOMATIC LOCALIZATION OF THE LEFT VENTRICLE IN CARDIAC CINE MAGNETIC RESONANCE IMAGING

(75) Inventors: Ying Sun, Singapore (SG); Jens Gühring, Monmouth Junction, NJ (US); Marie-Pierre Jolly, Hillsborough, NJ (US); Carmel Hayes, München (DE)

(73) Assignee: Siemens Aktiengesellschaft, München (DE)

( * ) Notice: Subject to any disclaimer, the term of this patent is extended or adjusted under 35 U.S.C. 154(b) by 612 days.

(21) Appl. No.: 12/396,534

(22) Filed: Mar. 3, 2009

(65) Prior Publication Data

US 2009/0290777 A1   Nov. 26, 2009

Related U.S. Application Data

(60) Provisional application No. 61/055,512, filed on May 23, 2008.

(51) Int. Cl.
  *G06K 9/00* (2006.01)
(52) U.S. Cl. .......................... 382/128; 382/131; 600/410
(58) Field of Classification Search .......................... None
  See application file for complete search history.

(56) References Cited

U.S. PATENT DOCUMENTS

| | | | |
|---|---|---|---|
| 6,898,302 B1* | 5/2005 | Brummer | 382/131 |
| 6,961,454 B2* | 11/2005 | Jolly | 382/131 |
| 7,864,997 B2* | 1/2011 | Aben | 382/128 |
| 2002/0168095 A1* | 11/2002 | Spreeuwers et al. | 382/131 |
| 2007/0253609 A1* | 11/2007 | Aben | 382/128 |
| 2008/0101676 A1* | 5/2008 | Zheng et al. | 382/131 |
| 2009/0080745 A1* | 3/2009 | Zheng et al. | 382/131 |

* cited by examiner

*Primary Examiner* — Hrayr A Sayadian
(74) *Attorney, Agent, or Firm* — Donald B. Paschburg; F. Chau & Associates, LLC (57) ABSTRACT

A method for automatically localizing left ventricle in medical image data includes acquiring a sequence of three-dimensional medical images spanning a cardiac cycle. Each of the images includes a plurality of two-dimensional image slices, one of which is defined as a template slice. The template slice of each medical image of the sequence is automatically cropped to include the heart and a margin around the heart based on temporal variations between pixels of the template slice throughout the sequence of medical images. The template slice of each medical image of the sequence is automatically contoured to determine the endo-cardial and epi-cardial boundaries for at least the end-diastolic and end-systolic phases. Localization information is generated for the left ventricle based on the determined endo-cardial and epi-cardial boundaries for at least the end-diastolic and end-systolic phases.

21 Claims, 7 Drawing Sheets

AUTOMATIC LOCALIZATION OF THE LEFT VENTRICLE IN CARDIAC CINE MAGNETIC RESONANCE IMAGING

CROSS-REFERENCE TO RELATED APPLICATION

The present application is based on provisional application Ser. No. 61/055,512, filed May 23, 2008, the entire contents of which are herein incorporated by reference.

BACKGROUND OF THE INVENTION

1. Technical Field

The present disclosure relates to magnetic resonance imaging (MRI) and, more specifically, to the automatic localization of the left ventricle in cardiac cine MRI.

2. Discussion of Related Art

Magnetic resonance imaging (MRI) is a medical imaging technique in which a human subject can be imaged in three-dimensions with a great deal of detail pertaining to the differentiation of different forms of bodily soft tissue. Thus MRI is well suited for the visualization and diagnosis of cardiovascular disease. In MRI, the human subject is exposed to a powerful magnetic field which aligns the nuclear magnetization of hydrogen atoms in water within bodily tissues. Radiofrequency fields are used to systematically alter the alignment of this magnetization and the hydrogen nuclei then produce a rotating magnetic field detectable by the scanner.

Structural image data may be generated from the received data signals to construct an image of the body. For example, the structural image may be generated from a number of spatial frequencies at different orientations. Frequency and phase encoding are used to measure the amplitudes of a range of spatial frequencies within the object being imaged. The number of phase-encoding steps performed may be selected to determine how much imaging data may be collected.

As MRI uses magnetic and radiofrequency fields to perform visualization, the patient is not exposed to potentially hazardous ionizing radiation as would be the case with CT scans.

Cardiac Cine MRI is the process by which multiple MR images are acquired in sequence over a period of time spanning one cardiac cycle. The result of cardiac cine MRI is a sequence of images that may form a moving picture showing how the heart pumps blood. Cardiac cine MRI may then be examined to assess ventricular function. For example, segmentation of the left ventricle may be used to measure the volume of blood in the left ventricle immediately before a contraction, an attribute known as the end-diastolic volume. Similarly, the volume of blood in the left ventricle at the end of contraction, an attribute known as end-systolic volume, may also be measured. The difference between end-diastolic and end-systolic volumes is the stroke volume, and represents the volume of blood ejected with each heart beat. The ejection fraction is the fraction of the end-diastolic volume that is ejected with each beat; which is the stroke volume divided by end-diastolic volume. The ejection fraction (EF) may have significant value in diagnosing cardiac disease.

According to the standard procedure for acquiring a cardiac cine MRI, the heart is imaged in three-dimensions using an MR scanner and the resulting image data is divided into short axis slices covering the left ventricle (LV) from the base of the heart to the apex. The image slices may then be analyzed using a semi-automatic segmentation tool that uses operator input to understand the structural features of the heart that are of diagnostic value, as the cardiac cycle progresses.

The level of operator input involved in performing the semi-automatic segmentation results in the procedure being time-consuming. Moreover, the quality of the results may be highly operator dependent and may be susceptible to human error.

SUMMARY

A method for automatically localizing left ventricle in medical image data includes acquiring a sequence of three-dimensional medical images spanning a cardiac cycle. Each of the images includes a plurality of two-dimensional image slices, one of which is defined as a template slice. The template slice of each medical image of the sequence is automatically cropped to include the heart and a margin around the heart based on temporal variations between pixels of the template slice throughout the sequence of medical images. The template slice of each medical image of the sequence is automatically contoured to determine the endo-cardial and epi-cardial boundaries for at least the end-diastolic and end-systolic phases. Localization information is generated for the left ventricle based on the determined endo-cardial and epi-cardial boundaries for at least the end-diastolic and end-systolic phases.

The sequence of three-dimensional medical images may be a cardiac cine MRI. The template slice may be defined for each three-dimensional medical image as the second or third image slice below a valve plane of the three-dimensional medical image. Automatically cropping and automatically contouring may be performed as part of an autolocalization step. The margin around the heart may be tight enough to avoid significant inclusion of the aorta and large enough to fully enclose the heart.

Automatic cropping may include performing an initial cropping, detecting the left-ventricle blood pool at the end-diastolic phase, and refining the initial cropping based on the detected left-ventricle blood pool to establish a final cropping.

The initial cropping may be based on a temporal intensity variation between corresponding pixels of the two-dimensional image slices at different cardiac phases wherein the initial cropping includes corresponding image pixels that have a relatively large standard deviation of intensity from cardiac phase to cardiac phase.

Detecting the left ventricle blood pool may include binarizing each template slice of each three-dimensional image at an end-diastolic phase wherein intensity values above a predetermined threshold, establishing one or more left-ventricle candidates as connected components of the binarized image, removing candidates that are relatively small in size, removing candidates that are relatively off-center with respect to the initial cropping, and choosing which of the remaining candidates represents the left-ventricle based on the application of one or more shape features.

Binarizing each template slice may include performing Gaussian clustering. The generated localization information for the left ventricle may be used to calculate measures characterizing ventricular function (e.g. stroke volume, ejection fraction, etc.).

A method for automatically localizing left ventricle in medical image data includes acquiring a cardiac cine magnetic resonance (MR) image sequence that includes a sequence of MR image frames at various phases of a cardiac cycle, each MR image being divided into a plurality of slices.

At least one slice of at least two frames, including end-diastolic frame and an end-systolic frame, are automatically cropped to include the heart and a margin around the heart based on temporal pixel intensity variations throughout the sequence of medical images. The at least one slice of the at least two frames are automatically contoured to determine the endo-cardial and epi-cardial boundaries for at least the end-diastolic and end-systolic phases. Localization information for the left ventricle is generated based on the determined endo-cardial and epi-cardial boundaries for at least the end-diastolic and end-systolic phases.

Automatic cropping may include performing an initial cropping, detecting the left-ventricle blood pool at the end-diastolic phase, and refining the initial cropping based on the detected left-ventricle blood pool to establish a final cropping.

The initial cropping may be based on a temporal intensity variation between corresponding pixels of the image slices at different cardiac phases wherein the initial cropping includes corresponding image pixels that have a relatively large standard deviation of intensity from cardiac phase to cardiac phase.

Detecting the left ventricle blood pool may include binarizing the at least one slice of the at least two frames at the end-diastolic phase wherein intensity values above a predetermined threshold, establishing one or more left-ventricle candidates as connected components of the binarized image, removing candidates that are relatively small in size, removing candidates that are relatively off-center with respect to the initial cropping, and choosing which of the remaining candidates represents the left-ventricle based on the application of one or more shape features.

Binarizing each of the at least one slice may include performing Gaussian clustering.

A computer system includes a processor and a program storage device readable by the computer system, embodying a program of instructions executable by the processor to perform method steps for automatically localizing left ventricle in medical image data. The method includes acquiring a cardiac cine magnetic resonance (MR) image sequence that includes a sequence of MR image frames at various phases of a cardiac cycle, each MR image being divided into a plurality of slices, one of which is defined as a template slice. The template slice of at least two frames, including end-diastolic frame and an end-systolic frame, are automatically cropped to include the heart and a margin around the heart based on temporal variations between pixels of the template slice throughout the sequence of medical images. The template slice of the at least two frames is automatically contoured to determine the endo-cardial and epi-cardial boundaries for at least the end-diastolic and end-systolic phases. Localization information is generated for the left ventricle based on the determined endo-cardial and epi-cardial boundaries for at least the end-diastolic and end-systolic phases.

Automatic cropping may include performing an initial cropping, detecting the left-ventricle blood pool at the end-diastolic phase, and refining the initial cropping based on the detected left-ventricle blood pool to establish a final cropping.

The initial cropping is based on a temporal intensity variation between corresponding pixels of the image slices at different cardiac phases wherein the initial cropping includes corresponding image pixels that have a relatively large standard deviation of intensity from cardiac phase to cardiac phase.

Detecting the left ventricle blood pool may include binarizing the template slices of the at least two frames at the end-diastolic phase wherein intensity values above a predetermined threshold, establishing one or more left-ventricle candidates as connected components of the binarized image, removing candidates that are relatively small in size, removing candidates that are relatively off-center with respect to the initial cropping, and choosing which of the remaining candidates represents the left-ventricle based on the application of one or more shape features.

Binarizing the template slices may include performing Gaussian clustering.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention seek to provide for automatic localization of the left ventricle (LV) in cardiac cine MR images so that diagnostic information may be quickly, accurately and consistently derived from the cardiac cine MR image data. The framework for performing automatic localization according to exemplary embodiments of the present invention may include performing segmentation during MR image reconstruction and automatic localization of the left ventricle from the cardiac cine MR images. In the course of performing automatic localization, the position and the size of the left ventricle may be understood so that the contours for endo- and epi-cardial boundaries may be properly initialized.

Figure 1:
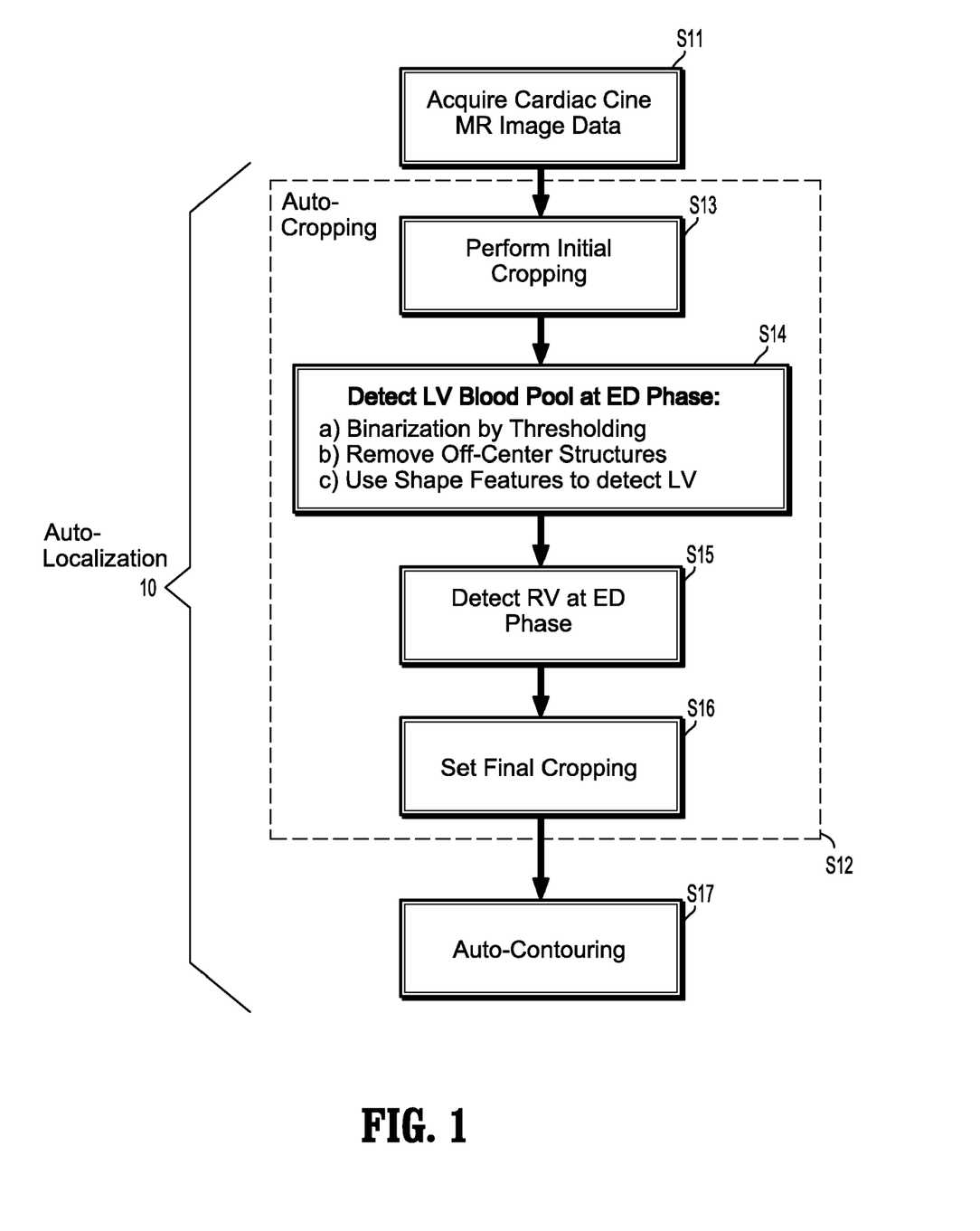
FIG. 1 is a flowchart illustrating a method for the automatic localization of the left ventricle (LV) in cardiac cine MR images according to an exemplary embodiment of the present invention.

FIG. 1 is a flowchart illustrating a method for the automatic localization of the left ventricle (LV) in cardiac cine MR images according to an exemplary embodiment of the present invention. First, the cardiac cine MR images may be acquired (Step S11). As discussed above, the cardiac cine MR images may include a sequence of images taken during a cardiac cycle. The image slices of the cardiac cine MR images may be acquired such that the first or second slice is in the valve plane and the subsequent slice is considered a template slice. Thus the template slice may be either the second or third image slice. Autolocalization 10 may then be applied to the MR images at the template slice for various phases of the cardiac cycle. Autolocalization 10 may include two steps, an auto-cropping step (Step S12) and an auto-contouring step (Step S17).

In the auto-cropping step (Step S12), a bounding box is drawn around the heart in the template slice for each phase of the cardiac cycle. Each bounding box should have an appropriately sized margin. The appropriately sized margin should be tight enough to avoid significant inclusion of the aorta as significant inclusion of the aorta may lead to the segmentation of the aorta, which is often visible in the cine images. The appropriately sized margin should also be large enough to fully enclose the heart, and especially the left ventricle, or the calculation of values of diagnostic relevance may be inaccurate.

Automatic cropping (Step S12) may include the following sub-steps: First initial cropping may be performed (Step S13). Since the heart experiences significant motion between image acquisition of the different cardiac phases, an initial cropping may be obtained based on temporal intensity variations between the images of different phases of the template slice. Thus as the image of the heart is likely to experience intensity variations as the cardiac cycle progresses, and the surrounding tissue is unlikely to experience intensity variations as a function of cardiac cycle, the initial cropping may be drawn to include those pixels that experience intensity variations over time.

To locate the intensity variations, the standard deviation of the intensity of each pixel across the image sequence may be calculated. Here, pixels having relatively large standard deviations may indicate motion. Accordingly, initial cropping may include pixels with relatively high standard deviations.

After initial cropping has been performed (Step S13), detection of the LV blood pool at the end-diastole (ED) phase may be performed (Step S14). To detect the blood pool, a binary image is obtained by thresholding the frame of the cine image data that represents the ED phase (Step S14a). In performing thresholding, each image pixel may be assigned a value of zero or one depending on whether the pixel intensity exceeds a particular threshold. It may be assumed that pixels above the threshold intensity level represent blood and pixels below the threshold intensity level do not represent blood. The threshold level for the blood may be set, for example, by Gaussian clustering. Small isolated connected components may be excluded from the blood pool as part of this step, as it may be assumed that the LV blood pool is comprised of large contiguous shapes.

After thresholding has been performed (Step S14a), off-center structures may be removed from being considered a candidate for being part of the LV (Step S14b). Here, location information may be used to eliminate off-center candidate regions prior to the detection of the LV as it may be assumed that the myocardium is located substantially centrally within the MR images of the cardiac study and is generally located close to the center of the initial cropping box, especially where the initial cropping box has been determined based on the standard deviation of pixel intensities across the frames of the image study.

Removal of the off-center structures may be performed, for example, based on location information relative to the initial cropping of the various connected components, which each represent candidate regions. Thus, regions that are either too far away from the image center or too close to the border of the initial cropping box may be dismissed as not corresponding to the LV.

Figure 2:
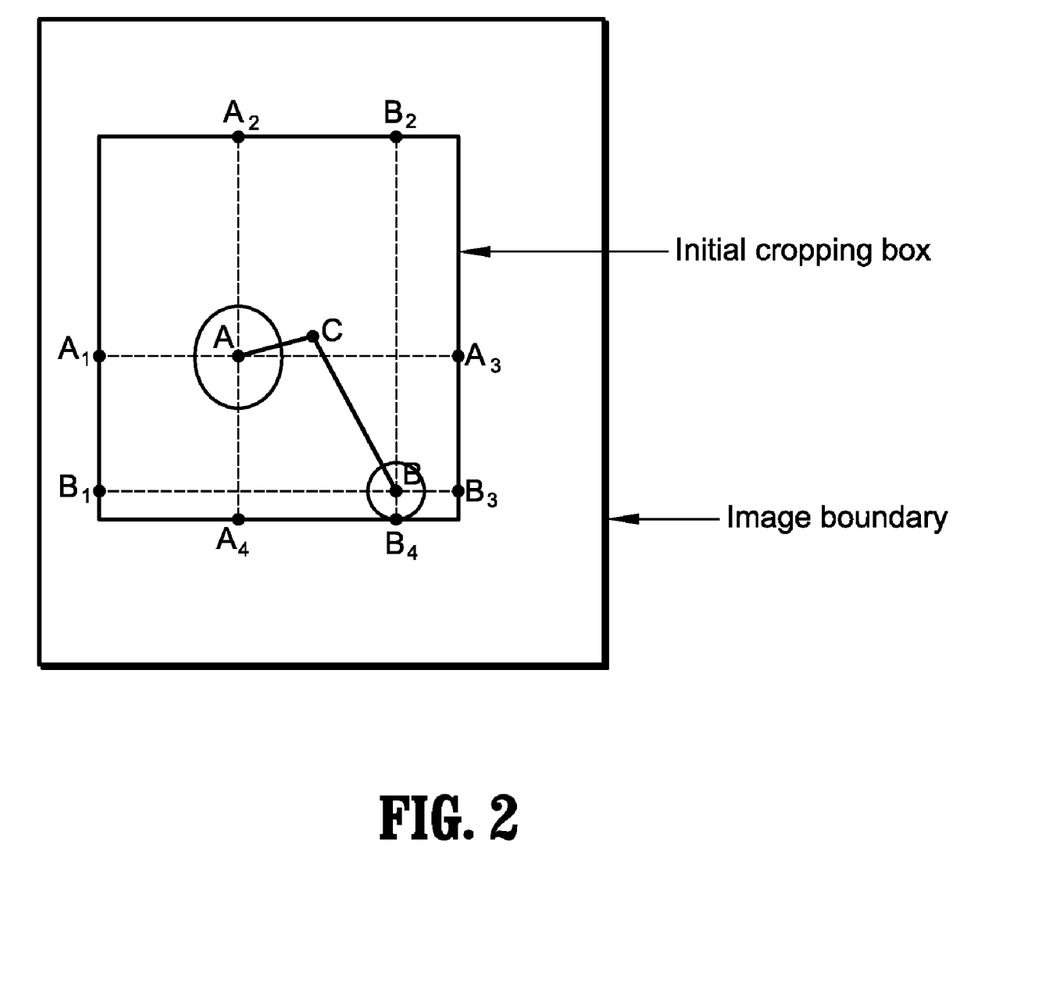
FIG. 2 is a diagram illustrating an approach for computing a degree of off-centerness of a candidate region according to an exemplary embodiment of the present invention.

Exemplary embodiments of the present invention provide a ratio that may be used to quantify the off-centerness of each candidate region with respect to the image and the initial cropping box. FIG. 2 is a diagram illustrating an approach for computing a degree of off-centerness of a candidate region according to an exemplary embodiment of the present invention. Here, "C" denotes the center point of the image; "A" represents the center of a first candidate region shown as the circle surrounding point "A." Points $A_1$, $A_2$, $A_3$, and $A_4$, represent the four corner points of intersection between the initial cropping box and orthogonal rays that are aligned with the cropping box and that are passing through the center point of the first candidate region "A." Also in this figure is a second candidate region "B" represented as the circle around the point "B" which represents the center of the second candidate region. Points $B_1$, $B_2$, $B_3$, and $B_4$, represent the four corner points of intersection between the initial cropping box and orthogonal rays that are aligned with the cropping box and that are passing through the center point of the second candidate region "B."

Here, $d_{AC}$ denotes the distance between points A and C, and similarly, the other terms d represent distances between the locations of the points represented by the subscript. The off-centerness of the candidate region centered around point A may be defined as the ratio between $d_{AC}$ and the minimum distance to the border of the initial cropping box. This ratio may be expressed in accordance with equation 1 below:

$$OC_A = \frac{d_{AC}}{\min(d_{AA_1}, d_{AA_2}, d_{AA_3}, d_{AA_4})} = \frac{d_{AC}}{d_{AA_1}} \quad (1)$$

Accordingly, the larger the distance of the candidate region is to the center of the image ($d_{AC}$) or the smaller the distance of the candidate region is to the border of the initial cropping box ($d_{AA_1}$), the higher the degree of off-centerness ($OC_A$).

The off-centerness may be calculated for each candidate region so that candidates with a degree of off-centerness that exceeds a predetermined threshold may be removed from consideration prior to identifying the LV. Thus, there may be a plurality of OC's calculated, one for each candidate region. The threshold may be determined, for example, in accordance with equation 2 below:

$$OC_{thresh} = \max(2 \cdot OC_{min}, 1) \quad (2)$$

where $OC_{thresh}$ is the threshold value and $O_{Cmin}$ is the minimum OC value of the various candidate regions. By setting the threshold value accordingly, off-center structures that may be otherwise heart-like in their appearance are not misidentified as the heart. For example, because circularity may be used as a shape feature in detecting the hear, there may be a possibility that a circular candidate may be mistakenly identified as the heart. By removing off-center candidates, the likelihood that a candidate is misidentified as the heart is reduced.

Next, as part of the detection of the LV blood pool, one or more shape features may be used to detect the LV (Step S14c). As the binary image may include multiple connected components, only one of which is likely to be the LV, the one or more shape features may be applied to each connected component of the binary image. A connected component is considered to be a contiguous grouping of pixels with a value of "one." Exemplary embodiments of the present invention may utilize shape features such as eccentricity, convexity, and circularity to assess the shape characteristics of each connected component and ultimately, to determine which of the connected components corresponds to the LV.

Here the eccentricity may be computed, for example, as the ratio between the minimum and maximum radii of the connected component in question. The convexity may be computed, for example, as the ratio between the total area of the connected component in question and the area of its convex hull. The circularity may be computed, for example, as the circularity of the convex hull, and may be defined as $4\pi$ times the area of the convex hull of the connected component in question over the square of its perimeter. It is assumed that the LV will correspond to the connected component that exhibits one or more of the following characteristics: least eccentric, most convex and having the highest circularity. Additionally, where two connected components have similar shape features, the larger connected component of the two may be favored as the LV to reduce the likelihood that the aorta is accidentally selected as the LV.

After detection of the LV blood pool at the (ED) phase has been performed (Step S14), in the next step, the right ventricle RV blood pool may be detected at the ED phase (Step S15). It may be assumed that the RV blood pool is represented by a connected component from the binary image that is proximate to the connected component identified as the LV in the prior step and of a size that is fairly large with respect to the other connected components. Based on these assumptions, the RV may be automatically identified.

Next, a final cropping may be set (Step S16). The final cropping may be implemented as a refinement of the initial cropping wherein the bounding box of the final cropping may be set precisely around an estimated myocardium boundary plus an appropriate margin that is set according to the estimated thickness of the myocardium as well as the area of the LV. The thickness of the myocardium may be estimated based on the detected LV and RV masks that have been established in the prior steps.

Figure 3:
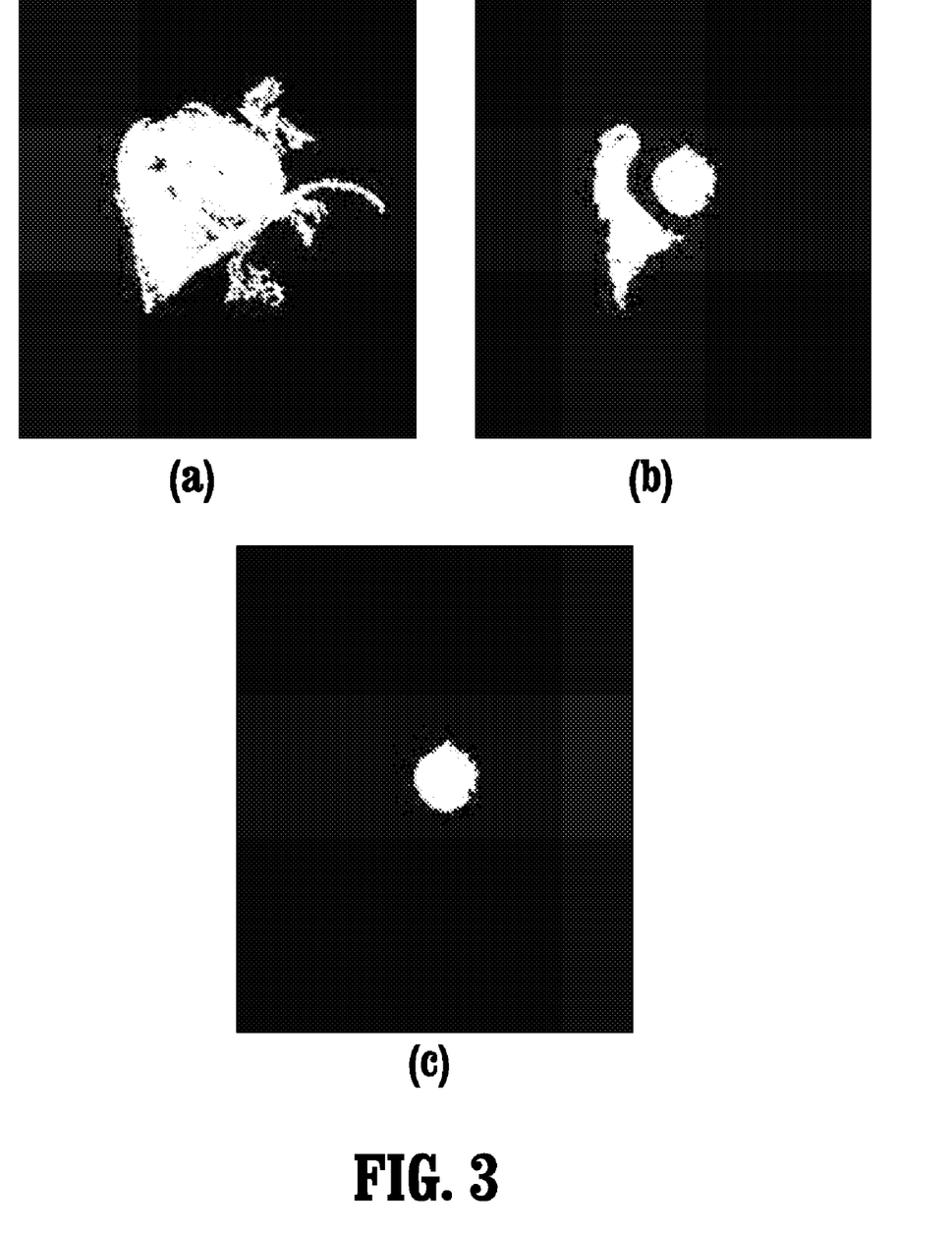
FIG. 3 is a set of exemplary images illustrating auto-cropping according to an exemplary embodiment of the present invention.
Figure 4A:
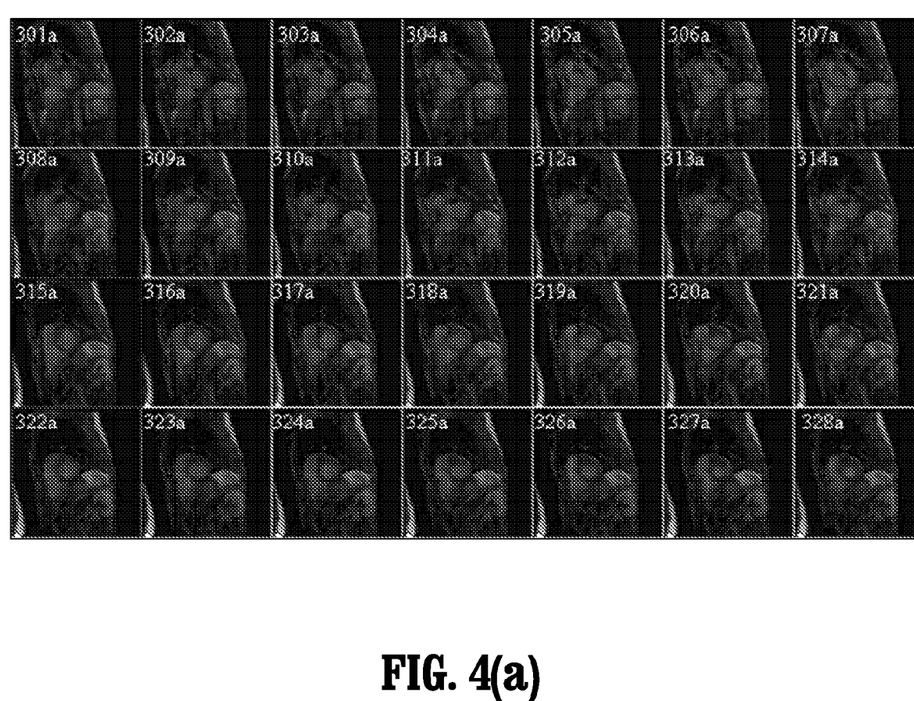
FIG. 4 is a set of exemplary images illustrating the effects of auto-cropping on cardiac cine MR images according to an exemplary embodiment of the present invention.
Figure 4B:
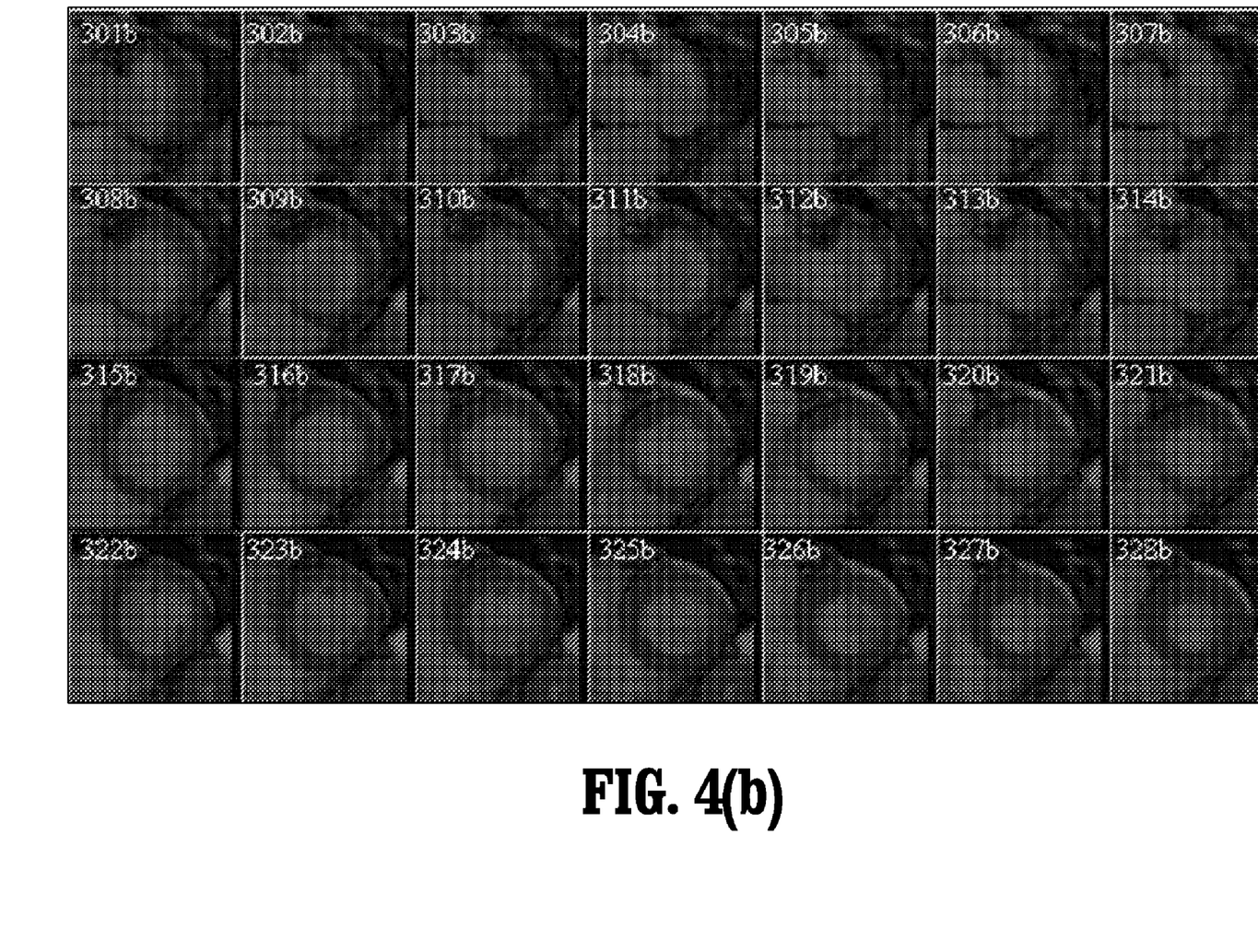

FIG. 3 is a set of exemplary images illustrating auto-cropping according to an exemplary embodiment of the present invention. FIG. 3a is a heart region detection representing the intensity variations that are used to calculate the initial cropping in Step S13. The intensity of each pixel in this image is determined by the standard deviation of the intensity of each corresponding pixel across the image sequence. Thus, the bright white areas of the image represent the structures that demonstrate movement over time, which is understood to be the heart. FIG. 3b shows the result of thresholding to obtain the connected components in Step 14a. Accordingly, here, the results of Gaussian clustering and cluster removal are shown. Off-center structures have been removed as well as described in Step 14b. FIG. 3c shows the result of identifying the LV region that is performed using shape features as performed in Step 14c FIGS. 4(a) and (b) are sets of exemplary images illustrating the effects of auto-cropping on cardiac cine MR images according to an exemplary embodiment of the present invention. In FIG. 4(a), a set of cardiac cine MR frames 301a-328a are shown. Frame 315a represents the template slice. In these image frames, the entire chest area can be seen. In FIG. 4(b), however, the set of auto-cropped cardiac cine MR frames 301b-328b are shown. Here, frame 315b represents the template slice. As can be seen from these frames, the images are precisely cropped to include only the LV region and an appropriately sized margin.

After auto-cropping has been completed (Step S12 and Steps S13-S16) auto-contouring may be performed (Step S17). In auto-contouring, the LV is detected in every phase of the cardiac cine MRI from the ED phase to the ES phase. This step may include, for example, starting from the template image and determining the contours of the endo- and epicardial boundaries at each phase. These two contours should appear as concentric circles as the heart has been imaged from the short axis in which the heart appears as a circle in each image slice. Here, the LV may be detected, for example, using the same approach as discussed above with respect to detecting the LV at the ED phase in auto-cropping. However, in this step, the checking criteria may be more discriminating with respect to the use of the shape features and the size constraints so that successful detection is more probable. In the event that detection fails to provide a result for the LV, an alternative, and perhaps more conventional, approach may be used to determine the LV. For example, a semi-automatic approach may be used as a fall-back approach.

Figure 5:
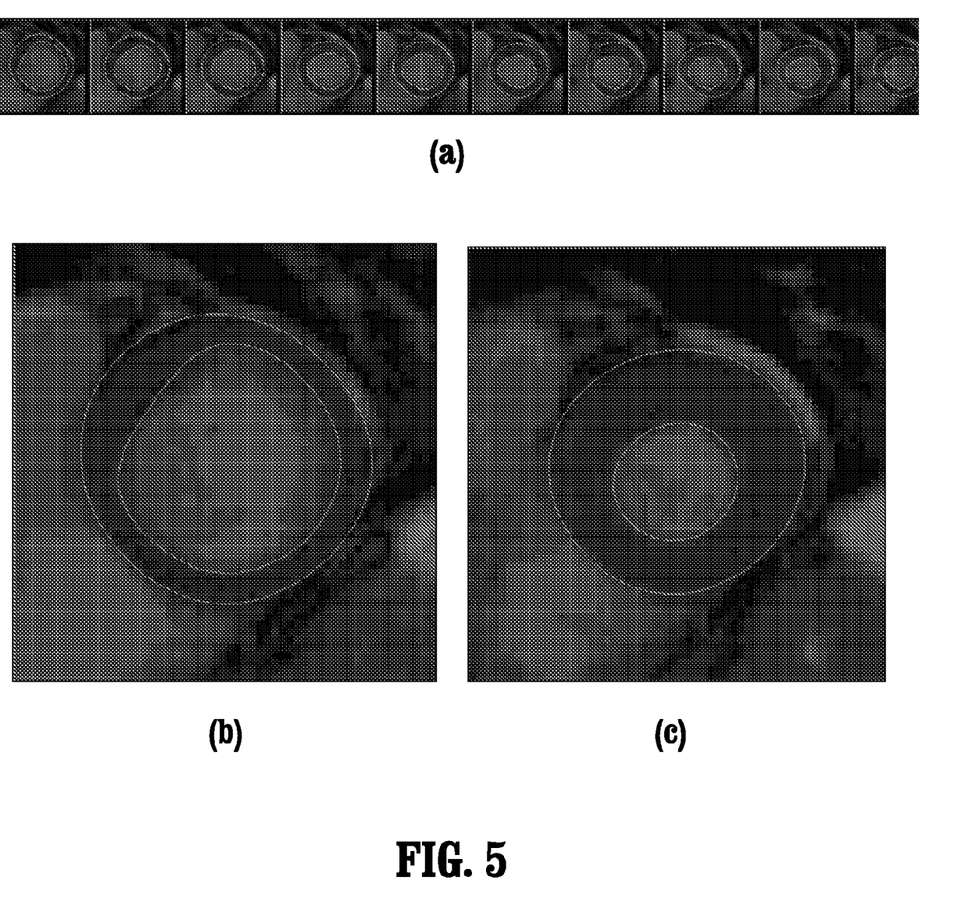
FIG. 5 is a set of exemplary images illustrating a result of automatic localization of the LV according to an exemplary embodiment of the present invention.

FIGS. 5(a)-(c) are exemplary images illustrating a result of automatic localization of the LV according to an exemplary embodiment of the present invention. In these figures, the segmentation results of the template slice is shown over time. FIG. 5(a) shows a sequence of cardiac cine MR image frames. FIG. 5(b) shows an image frame at the ED phase and FIG. 5(c) shows an image frame at the ES phase. As can be seen in these images, two concentric contours are overlaid over the cropped template sequence. The outer contour represents the outer boundary of the myocardium surrounding the LV and the inner contour represents the blood pool of the LV. The ejection fraction may be calculated by comparing the volume of the inner contour at both the ED phase and the ES phase.

Figure 6:
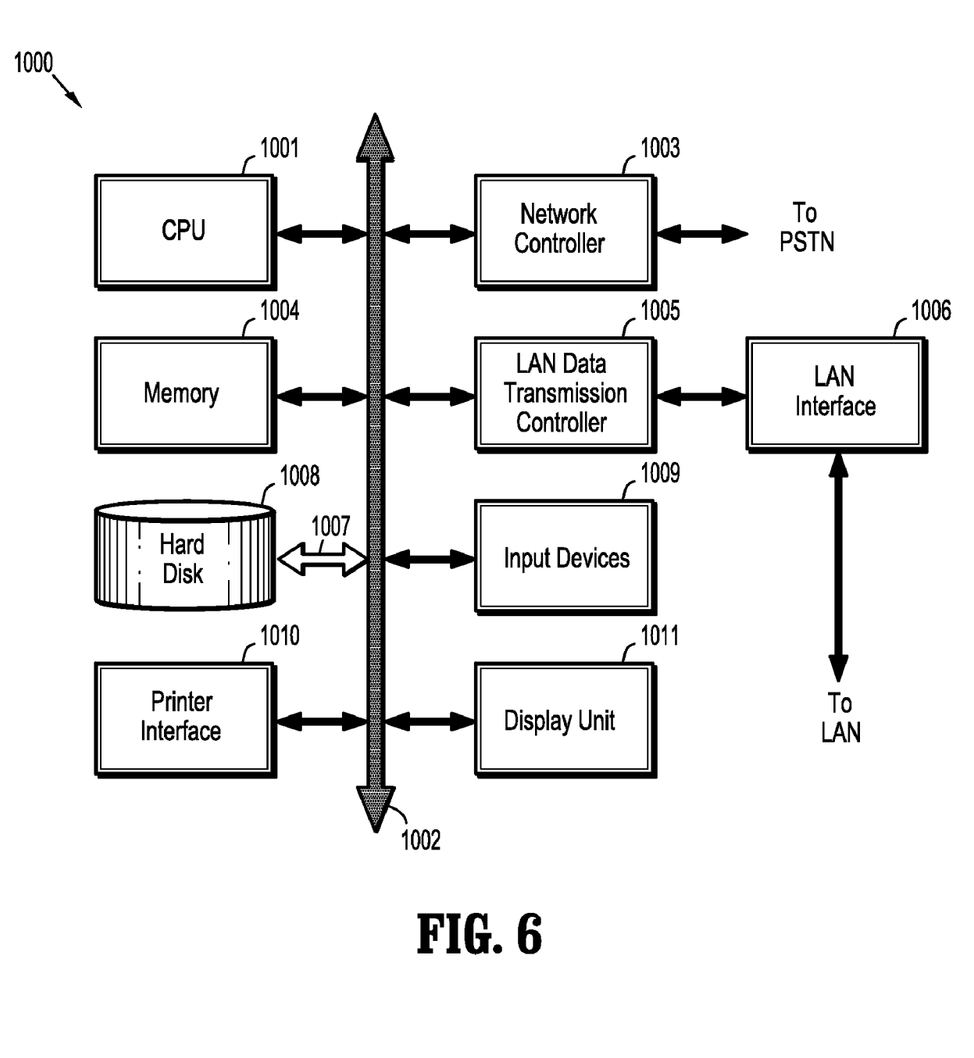
FIG. 6 shows an example of a computer system capable of implementing the method and apparatus according to embodiments of the present disclosure.

FIG. 6 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for automatically localizing left ventricle in medical image data, comprising the computer implemented steps of:
acquiring a sequence of three-dimensional medical images spanning a cardiac cycle, each including a plurality of two-dimensional image slices, one of which is defined as a template slice;
automatically cropping the template slice of each medical image of the sequence to include the heart and a margin around the heart based on temporal variations between pixels of the template slice throughout the sequence of medical images;

automatically contouring the template slice of each medical image of the sequence to determine the endo-cardial and epi-cardial boundaries for at least the end-diastolic and end-systolic phases; and generating localization information for the left ventricle based on the determined endo-cardial and epi-cardial boundaries for at least the end-diastolic and end-systolic phases.

2. The method of claim 1, wherein the sequence of three-dimensional medical images is a cardiac cine MRI.

3. The method of claim 1, wherein the template slice is defined for each three-dimensional medical image as a particular slice below a valve plane of the three-dimensional medical image.

4. The method of claim 1, wherein the steps of automatically cropping and automatically contouring are performed as part of an autolocalization step.

5. The method of claim 1, wherein the margin around the heart tight enough to avoid inclusion of the aorta and large enough to fully enclose the heart.

6. The method of claim 1, wherein automatic cropping includes:

performing an initial cropping;

detecting the left-ventricle blood pool at the end-diastolic phase; and refining the initial cropping based on the detected left-ventricle blood pool to establish a final cropping.

7. The method of claim 6, wherein the initial cropping is based on a temporal intensity variation between corresponding pixels of the two-dimensional image slices at different cardiac phases.

8. The method of claim 7, wherein the initial cropping includes corresponding image pixels that have a large standard deviation of intensity from cardiac phase to cardiac phase.

9. The method of claim 6, wherein detecting the left ventricle blood pool includes:

binarizing each template slice of each three-dimensional image at an end-diastolic phase wherein intensity values above a predetermined threshold;

establishing one or more left-ventricle candidates as connected components of the binarized image;

removing candidates that are small in size;

removing candidates that are off-center with respect to the initial cropping; and choosing which of the remaining candidates represents the left-ventricle based on the application of one or more shape features.

10. The method of claim 9, wherein binarizing each template slice includes Gaussian clustering.

11. The method of claim 1, wherein the generated localization information for the left ventricle is used to characterize left ventricle function.

12. A method for automatically localizing left ventricle in medical image data, comprising the computer implemented steps of:

acquiring a cardiac cine magnetic resonance (MR) image sequence that includes a sequence of MR image frames at various phases of a cardiac cycle, each MR image being divided into a plurality of slices;

automatically cropping at least one slice of at least two frames, including end-diastolic frame and an end-systolic frame, to include the heart and a margin around the heart based on temporal pixel intensity variations throughout the sequence of medical images;

automatically contouring the at least one slice of the at least two frames to determine the endo-cardial and epi-cardial boundaries for at least the end-diastolic and end-systolic phases; and generating localization information for the left ventricle based on the determined endo-cardial and epi-cardial boundaries for at least the end-diastolic and end-systolic phases.

13. The method of claim 12, wherein automatic cropping includes:

performing an initial cropping;

detecting the left-ventricle blood pool at the end-diastolic phase; and refining the initial cropping based on the detected left-ventricle blood pool to establish a final cropping.

14. The method of claim 13, wherein the initial cropping is based on a temporal intensity variation between corresponding pixels of the image slices at different cardiac phases.

15. The method of claim 13, wherein detecting the left ventricle blood pool includes:

binarizing the at least one slice of the at least two frames at the end-diastolic phase wherein intensity values above a predetermined threshold;

establishing one or more left-ventricle candidates as connected components of the binarized image;

removing candidates that are small in size;

removing candidates that are off-center with respect to the initial cropping; and choosing which of the remaining candidates represents the left-ventricle based on the application of one or more shape features.

16. The method of claim 15, wherein binarizing each of the at least one slice includes performing Gaussian clustering.

17. A computer system comprising:

a processor; and a program storage device readable by the computer system, embodying a program of instructions executable by the processor to perform method steps for automatically localizing left ventricle in medical image data, the method comprising:

acquiring a cardiac cine magnetic resonance (MR) image sequence that includes a sequence of MR image frames at various phases of a cardiac cycle, each MR image being divided into a plurality of slices, one of which is defined as a template slice;

automatically cropping the template slice of at least two frames, including end-diastolic frame and an end-systolic frame, to include the heart and a margin around the heart based on temporal variations between pixels of the template slice throughout the sequence of medical images;

automatically contouring the template slice of the at least two frames to determine the endo-cardial and epi-cardial boundaries for at least the end-diastolic and end-systolic phases; and generating localization information for the left ventricle based on the determined endo-cardial and epi-cardial boundaries for at least the end-diastolic and end-systolic phases.

18. The computer system of claim 17, wherein automatic cropping includes:

performing an initial cropping;

detecting the left-ventricle blood pool at the end-diastolic phase; and refining the initial cropping based on the detected left-ventricle blood pool to establish a final cropping.

19. The computer system of claim 18, wherein the initial cropping is based on a temporal intensity variation between corresponding pixels of the image slices at different cardiac phases wherein the initial cropping includes corresponding image pixels that have a large standard deviation of intensity from cardiac phase to cardiac phase.

20. The computer system of claim 18, wherein detecting the left ventricle blood pool includes:
 binarizing the template slices of the at least two frames at the end-diastolic phase wherein intensity values above a predetermined threshold;
 establishing one or more left-ventricle candidates as connected components of the binarized image;
 removing candidates that are small in size;
 removing candidates that are off-center with respect to the initial cropping; and
 choosing which of the remaining candidates represents the left-ventricle based on the application of one or more shape features.

21. The computer system of claim 20, wherein binarizing the template slices includes performing Gaussian clustering.

* * * * *